(12) United States Patent
Gomaa et al.

(10) Patent No.: US 8,403,995 B2
(45) Date of Patent: *Mar. 26, 2013

(54) DEVICE AND METHOD FOR DETERMINING PROPER SEATING OF AN ORTHOPAEDIC PROSTHESIS

(75) Inventors: Said Gomaa, Fort Wayne, IN (US); Jason Sherman, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 161 days.

This patent is subject to a terminal disclaimer.

(21) Appl. No.: 12/820,762

(22) Filed: Jun. 22, 2010

(65) Prior Publication Data

US 2010/0262256 A1    Oct. 14, 2010

Related U.S. Application Data

(63) Continuation-in-part of application No. 12/338,510, filed on Dec. 18, 2008, now Pat. No. 8,075,629.

(51) Int. Cl.
*A61F 2/32* (2006.01)
(52) U.S. Cl. ................................... 623/22.21
(58) Field of Classification Search ............. 623/22.11, 623/22.21–22.39
See application file for complete search history.

(56) References Cited

U.S. PATENT DOCUMENTS

| | | |
|---|---|---|
| 3,745,995 A | 7/1973 | Kraus |
| 5,141,512 A | 8/1992 | Farmer et al. |
| 5,318,571 A | 6/1994 | Benson |
| 5,702,476 A | 12/1997 | Limacher et al. |
| 5,755,794 A | 5/1998 | Benson |
| 5,824,078 A | 10/1998 | Nelson et al. |
| 5,981,828 A | 11/1999 | Nelson et al. |
| 6,293,971 B1 | 9/2001 | Nelson et al. |
| 6,302,890 B1 | 10/2001 | Leone, Jr. |
| 6,623,488 B1 | 9/2003 | Leone, Jr. |
| 2002/0049394 A1 | 4/2002 | Roy et al. |
| 2004/0172502 A1 | 9/2004 | Lionetta et al. |
| 2005/0010302 A1 | 1/2005 | Dietz et al. |
| 2006/0047283 A1 | 3/2006 | Evans, III et al. |
| 2006/0190011 A1 | 8/2006 | Ries |
| 2007/0179739 A1 | 8/2007 | Donofrio et al. |
| 2008/0306486 A1 | 12/2008 | Lye |

FOREIGN PATENT DOCUMENTS

| | | |
|---|---|---|
| CA | 2 148 657 A1 | 11/1996 |
| CA | 2 250 446 | 6/1999 |
| DE | 19932242 A1 | 1/2000 |
| EP | 0 327 509 B1 | 8/1989 |

(Continued)

OTHER PUBLICATIONS

Extended European Search Report, European Application No. 10196769.3-2310, May 3, 2011, 5 pages.

(Continued)

*Primary Examiner* — Thomas J Sweet
*Assistant Examiner* — Jason-Dennis Stewart
(74) *Attorney, Agent, or Firm* — Barnes & Thornburg LLP

(57) ABSTRACT

An orthopaedic prosthesis includes a curved outer surface configured to abut a patient's bone when the orthopaedic prosthesis is implanted therein. The outer surface may or may not be electrically conductive. A channel is defined in the outer surface in which one or more electrical conductors are positioned. A switch is positioned at a first location on the outer surface and is configured to establish an electrical connection between the electrical conductor and the outer surface (e.g., an electrical trace) and/or another electrical conductor when the first location of the outer surface is pressed against the patient's bone. The switch may be embodied as an end of the electrical conductor or a more complex switch such as a push-button type switch.

16 Claims, 11 Drawing Sheets

FOREIGN PATENT DOCUMENTS

| | | |
|---|---|---|
| EP | 0353171 | 1/1990 |
| EP | 0 807 426 A2 | 11/1997 |
| EP | 1 835 967 A1 | 9/2007 |
| FR | 2649005 | 1/1991 |
| IE | 880739 | 3/1990 |
| JP | 63318939 A | 12/1988 |
| JP | 2000325374 A | 11/2000 |
| NZ | 548764 A | 12/2007 |
| WO | 2006/060632 A1 | 6/2006 |
| WO | 2006/109983 A1 | 10/2006 |
| WO | 2007/056810 A1 | 5/2007 |
| WO | 2008089723 | 7/2008 |

OTHER PUBLICATIONS

European Search Report, European Application No. 11169970.8-2310, Sep. 9, 2011, 7 pages.

European Search Report for European Patent Application No. 09178127.8-2310, Apr. 22, 2010, 5 pgs.

DEVICE AND METHOD FOR DETERMINING PROPER SEATING OF AN ORTHOPAEDIC PROSTHESIS

CROSS-REFERENCE TO RELATED U.S. PATENT APPLICATION

This application is a continuation-in-part application of U.S. Pat. No. 8,075,629 entitled "ORTHOPAEDIC PROSTHESIS HAVING A SEATING INDICATOR," which was filed on Dec. 18, 2008, the entirety of which is hereby incorporated by reference.

TECHNICAL FIELD

The present disclosure relates generally to orthopaedic prostheses and particularly to orthopaedic prostheses having an indicator coupled thereto for providing an indication when the prosthesis is properly seated.

BACKGROUND

Orthopaedic prostheses are implanted in patients by orthopaedic surgeons to, for example, correct or otherwise alleviate bone and/or soft tissue loss, trauma damage, and/or deformation of the bone(s) of the patients. Orthopaedic prostheses replace a portion of or the complete joint of a patient. For example, the orthopaedic prosthesis may replace the patient's hip, shoulder, ankle, knee or other joint. In the case of a hip replacement, the orthopaedic prosthesis includes an acetabular cup, which is secured to the surgically-prepared acetabulum of the patient. The acetabular cup replaces the natural bearing surface of the acetabulum with a new bearing surface for the natural or prosthetic head of the patient's femur.

During the orthopaedic surgical procedure, a surgeon initially prepares the patient's bone to receive the orthopaedic prosthesis. For example, in the case of a hip orthopaedic surgical procedure, the surgeon may initially ream the patient's acetabulum. The orthopaedic prosthesis is subsequently coupled to the patient's surgically-prepared bone. Depending on the particular orthopaedic surgical procedure, the type of orthopaedic prosthesis, and/or other factors, it may be difficult for the surgeon to determine when the orthopaedic prosthesis is fully seated into the patient's bone. For example, it may be difficult for the orthopaedic surgeon to visually confirm when particular portions of the orthopaedic prosthesis have contacted the patient's bone.

SUMMARY

According to one aspect, an acetabular cup includes an outer surface, an electrical conductor, an electrically conductive trace formed on the outer surface, and a switch. The outer surface may be configured to confront a portion of a patient's acetabulum when the acetabular cup is implanted in the patient. The outer surface may include a channel defined therein. The electrical conductor may be positioned in the channel. The switch may be located at a first location on the outer surface. The switch may have a first state wherein an electrical connection between the electrical conductor and the electrically conductive trace is broken and a second state wherein an electrical connection between the electrical conductor and the electrically conductive trace is established.

In some embodiments, the electrically conductive trace is located in the channel of the outer surface. Additionally, in some embodiments, the electrically conductive trace may include an electrically conductive pad formed on the outer surface at the first location. The electrically conductive trace may extend from the first location to a rim of the outer surface in some embodiments. Additionally, in some embodiments, the electrical conductor has a first end located in the channel toward a rim of the outer surface. Alternatively, in other embodiments, the first end may extend out of the channel at the rim of the outer surface. In some embodiments, the channel may extend from the first location to the rim of the outer surface.

In some embodiments, the switch may be embodied as a second end of the electrical conductor. In such embodiments, the second end of the electrical conductor may extend out of the channel at the first location of the outer surface and may be positionable such that the second end comes into contact with the electrically conductive trace when the first location of the outer surface is pressed against the patient's acetabulum. In some embodiments, the switch is configured such that the switch is positioned in the second state when the first location of the outer surface is pressed against the patient's acetabulum.

In some embodiments, the switch may be embodied as a push-button switch. In such embodiments, the push-button switch being may be biased to the first state. Additionally, the push-button switch may be configured such that the push-button switch is positioned in the second state when the first location of the outer surface is pressed against the patient's acetabulum.

According to another aspect, an acetabular cup may include an outer surface configured to confront a portion of a patient's acetabulum when the acetabular cup is implanted in the patient and an electrical conductor assembly. The outer surface may include a channel defined therein and the electrical conductor assembly may be positioned in the channel. The electrical conductor assembly may include a first conductor and a second conductor. Each of the first and second conductors may have a first end extending out of the channel at a first location on the outer surface. The first ends of the first and second conductors may form a switch having a first state wherein an electrical connection between the first and second conductors is broken and a second state wherein an electrical connection between the first and second conductors is established.

In some embodiments, the first conductor may be embodied as a wire and the second conductor may be embodied as a shielding formed around the wire. The second conductor may be secured to the outer surface at the first location in some embodiments. For example, in some embodiments, the outer surface may include an electrically conductive pad formed thereon. The second conductor may be electrically connected to the electrically conductive pad.

In some embodiments, each of the first and second conductors may include a second end opposite the first end. The second ends of the first and second conductors may be located in the channel. Additionally, in some embodiments, the switch may be configured such that the switch is positioned in the second state when the first location of the outer surface is pressed against the patient's acetabulum.

According to a further aspect, a method for implanting an acetabular cup in a patient may include placing the acetabular cup in an acetabulum of the patient and measuring a circuit parameter of a circuit secured to the acetabular cup. The circuit parameter may be measured by, for example, measuring a time constant of the circuit. Additionally or alternatively, the circuit parameter may be measured by, for example, measuring an impedance of the circuit. Additionally or alternatively, the circuit parameter may be measured by, for example, determining the state of a switch of the circuit.

BRIEF DESCRIPTION OF THE DRAWINGS

The detailed description particularly refers to the following figures, in which.

DETAILED DESCRIPTION OF THE DRAWINGS

Figure 1:
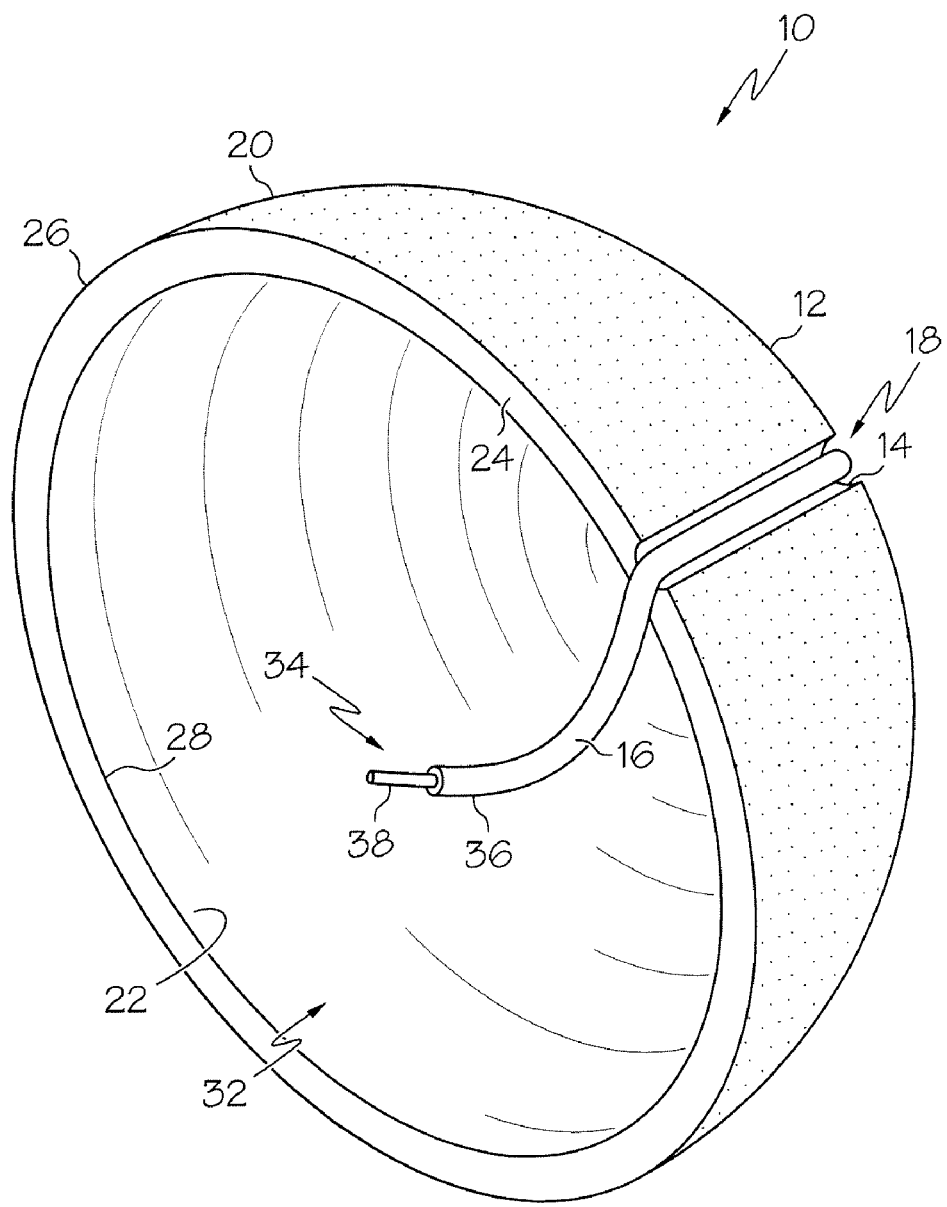
FIG. 1 is a perspective view of one embodiment of an orthopaedic prosthesis having a seating indicator coupled thereto.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring to FIG. 1, in one embodiment, an orthopaedic prosthesis 10 includes a curved outer surface 12 having a channel 14 defined therein, an electrical conductor 16 positioned in the channel 14, and a switch 18 positioned at a location of the curved outer surface 12 and electrically coupled to the electrical conductor 16. In the illustrative embodiment, the orthopaedic prosthesis 10 is embodied as an acetabular cup 20, but may be embodied as other prostheses in other embodiments. For example, the orthopaedic prosthesis 10 may be embodied as any orthopaedic prosthesis having a curved outer surface, such as a shoulder or ankle prosthesis, which can present difficulties for an orthopaedic surgeon to determine whether the prosthesis is properly seated into the patient's bone (e.g., when particular portions of the prosthesis 10 contact the patient's bone) due to visual limitations. Accordingly, although the orthopaedic prosthesis 10 is discussed in detail below in regard to an acetabular cup 20, it should be appreciated that such features and description may be equally applicable to other orthopaedic prostheses including shoulder and ankle prostheses.

The acetabular cup 20 includes the curved outer surface 12, a curved inner surface 22, and a rim surface 24 extending from the edge or rim 26 of the curved outer surface 12 to the edge or rim 28 of the curved inner surface 22. The acetabular cup 20 may be formed from any suitable material capable of being secured to the acetabulum of a patient and supporting a natural or artificial head portion of the patient's femur. For example, the acetabular cup 20 may be formed from a ceramic material, a polymer material, a titanium alloy, or other implantable metal material. The illustrative acetabular cup 20 is a monoblock prosthesis formed of a single piece and configured to be implanted into the patient's acetabulum without the use of bone cement. As such, the illustrative acetabular cup 20 does not include mounting holes defined through the inner and outer surfaces 12, 22, respectively. However, in some embodiments, the acetabular cup 20 may include any number of mounting holes, which are commonly used with bone screws to secure the cup 20 to the patient's bone.

In other embodiments, the acetabular cup 20 may be formed from a number of separate parts. For example, in some embodiments, the acetabular cup 20 may include a bearing 30 (see FIG. 2) configured to be received in a cavity 32 defined by the inner curved surface 22. In such embodiments, the bearing 30 provides an artificial surface on which the natural or artificial head portion of the femur of the patient may articulate. The bearing 30 may be formed from any material suitable for such purpose. For example, the bearing 30 may be formed from a metallic material, a ceramic material, a polymeric material such as polyethylene or ultra-high molecular weight polypropylene (UHMWPE), and/or the like.

In the illustrative embodiment, the curved outer surface 12 is electrically conductive. For example, in some embodiments, the curved outer surface 12 may have an electrical conductivity of 5 siemens per meter or greater. In embodiments wherein acetabular cup 20 is formed from a non-electrically conductive material, such as a ceramic or polymer material, the acetabular cup 20 may include an electrically conductive coating or texture applied to the outer surface 12 so as to form the electrically conductive outer surface 12. In some embodiments, the conductive coating may be configured to also enhance bone growth. Additionally, even in embodiments wherein the acetabular cup 20 is formed from an electrically conductive material, such as a metallic material, the electrically conductive coating may also be applied to the outer surface 12 of the cup 20.

Figure 2:
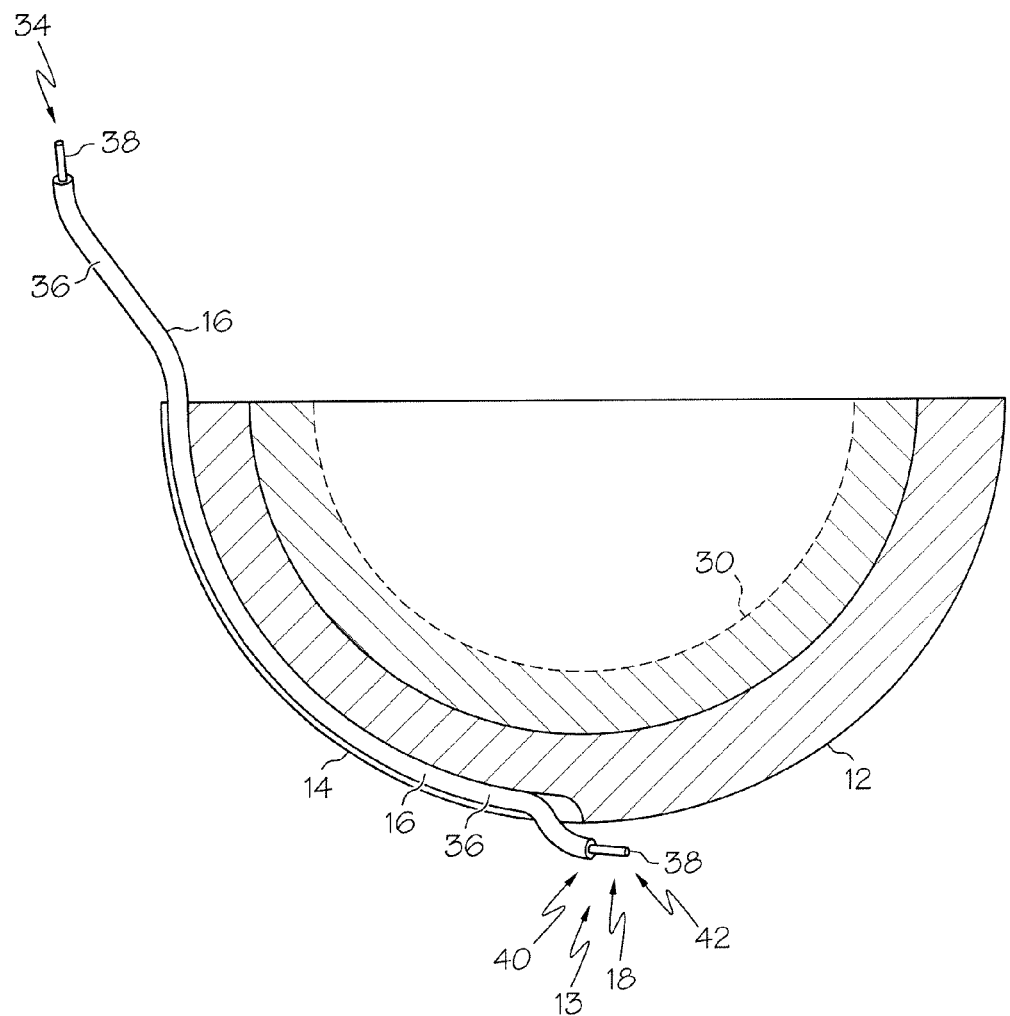
FIG. 2 is a cross-sectional view of the orthopaedic prosthesis of FIG. 1.
Figure 3:
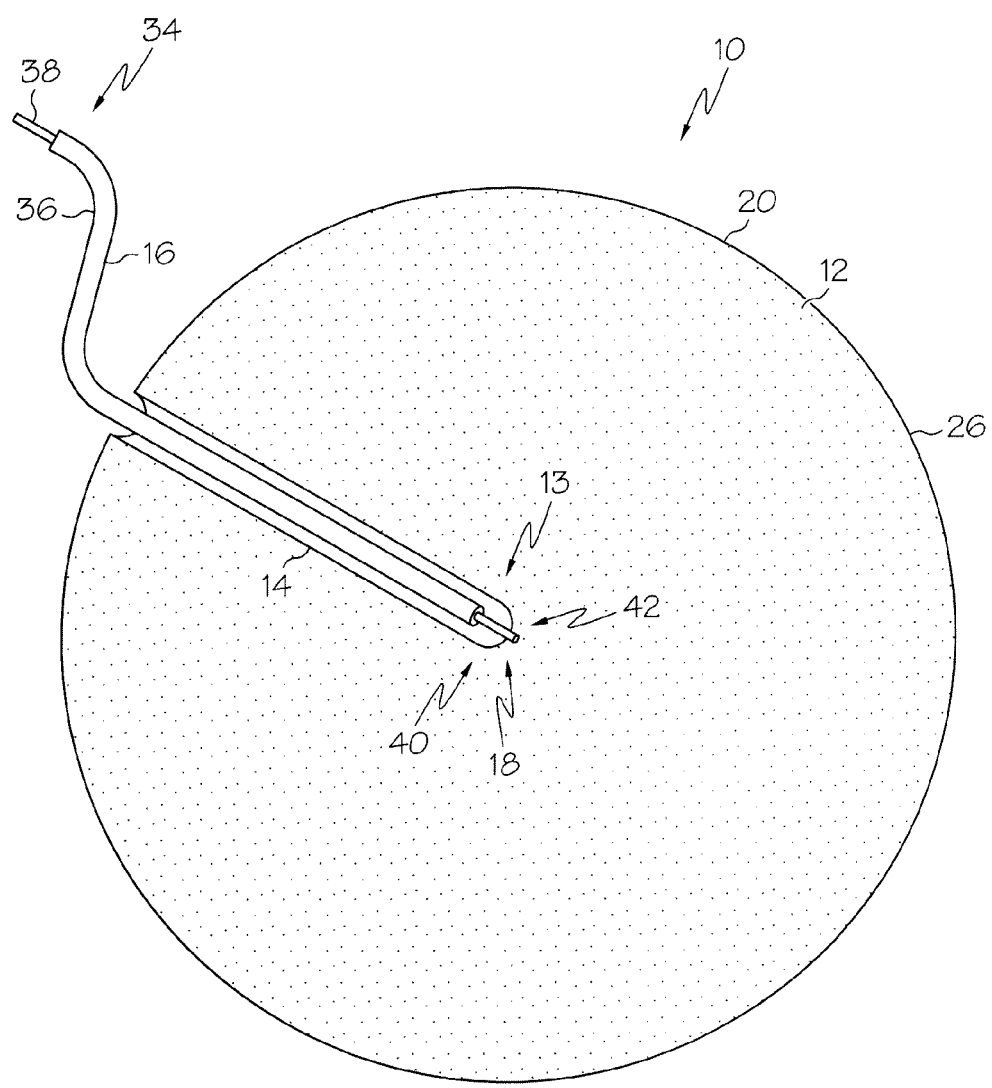
FIG. 3 is a plan view of the outer surface of the orthopaedic prosthesis of FIG. 1.
Figure 4:
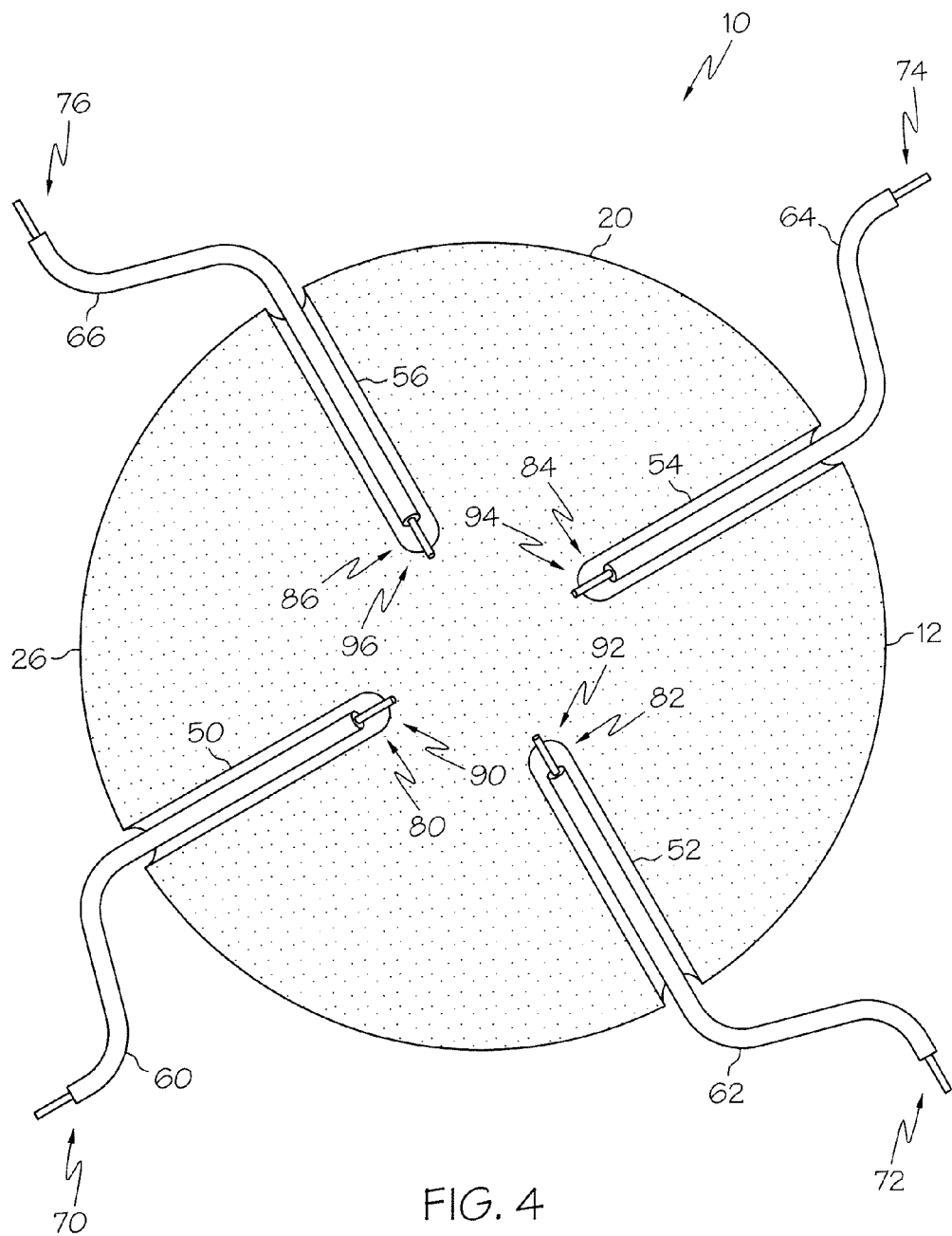
FIG. 4 is a plan view of the outer surface of another embodiment of the orthopaedic prosthesis of FIG. 1.

As discussed above, the outer surface 12 of the acetabular cup 20 includes the channel 14 defined therein. The channel 14 extends from the rim 26 of the outer surface 12 to a predetermined location 13 of the outer surface 12. The location 13 to which the channel 14 extends may be any location of interest on the outer surface 12 that contacts the patient's bone when the acetabular cup 20 is properly seated therein. For example, as illustrated in FIGS. 2 and 3, in some embodiments, the channel 14 may extend from the rim 26 to a location of the outer surface 12 substantially corresponding to the apex of the dome-shaped outer surface 12.

The electrical conductor 16 is positioned in the channel 14 and includes a first end 34 that extends out of the channel 14 at the rim 26 of the outer surface 12. In the illustrative embodiment, the electrical conductor 16 extends out of the channel 14 a length sufficient enough such that the electrical conductor 16 may be grasped by an orthopaedic surgeon while the acetabular cup 20 is fully seated into the patient's bone.

In the illustrative embodiment, the electrical conductor 16 is embodied as a wire, but may be embodied as other types of electrical conductors in other embodiments such as an electrical trace, rod, or other electrically conductive path. The electrical conductor 16 illustratively includes a non-electrically conductive cladding 36 and an electrically conductive inner core 38, which is surrounded by the cladding 36. In one particular embodiment, the cladding 36 is formed from a non-electrically conductive polymer cladding and the electrically conductive inner core 38 is formed from an electrically conductive polymer. However, the electrical conductor 16 may be formed from other bio-compatible materials in other embodiments. The cladding 36 provides an amount of electrical isolation to the inner core 38. To access the inner core 38, the cladding 36 may be stripped back or otherwise removed such that the inner core 38 extends therefrom as illustrated at the first end 34 of the electrical conductor 16 in FIG. 1.

The electrical conductor 16 may be held in place in the channel 14 via friction or via use of an adhesive. For example, in some embodiments, the channel 14 may have a width slightly larger than the outer width of the cladding 36 such that the electrical conductor 16 may be pressed into the channel 14 and held in place via frictional forces. Alternatively, a bio-compatible adhesive may be used to secure the electrical conductor 16 in the channel 14. In some embodiments, the adhesive may be semi-permanent such that the electrical conductor 16 may be removed from the channel 14 via application of an appropriate amount of force as discussed below in regard to FIG. 8.

As shown in FIG. 2, the switch 18 is positioned at the predetermined location 13 of the curved outer surface 12 (i.e., the location of interest that contacts the patient's bone when the cup 20 is properly seated). In the illustrative embodiment, the switch 18 is positioned near the apex of the dome-shaped outer surface 12. The switch 18 may be a simple switch or a complex switch. For example, in the illustrative embodiment, the switch 18 is embodied as a second end 40 of the electrical conductor 16. However, in other embodiments as discussed in more detail below in regard to FIGS. 5 and 6, the switch 18 may be embodied as a more complex switch that is electrically coupled to electrical conductor 16.

The illustrative switch 18 illustrated in FIGS. 1-4 is formed from the second end 40 of the electrical conductor 16 by removal of the non-conductive cladding 36, which exposes an end 42 of the inner core 38. The end 42 of the inner core 38 is positioned to extend out of the channel 14 and over a portion of the electrically conductive outer surface 12 without contacting the surface 12. However, when the acetabular cup 20 is properly seated in the patient's acetabulum, the end 42 of the inner core 38 is pressed against the electrically conductive outer surface 12 by the patient's bone thereby establishing a connection between the electrical conductor 16 and the outer surface 12.

As such, the switch 18 includes two states, a non-conductive state and a conductive state. In the first state, the end 42 of the inner core 38 is spaced apart from the electrically conductive outer surface 12 and no electrical connection is established between the electrical conductor 16 and the outer surface 12. The switch 18 is positioned in the first state prior to implantation of the acetabular cup 20. In the second state, the end 42 of the inner core 38 is in contact with the electrically conductive outer surface 12 and an electrical connection is established between the electrical conductor 16 and the outer surface 12. As such, as discussed in more detail below, an orthopaedic surgeon may determine whether the acetabular cup 20 is properly seated (i.e., whether the predetermined location 13 of the outer surface 12 is in contact with the patient's bone) by measuring the resistance between the outer surface 12 of the acetabular cup 20 and the first end 34 of the electrical conductor. A measured resistance value less than a predetermined threshold value is indicative of proper seating of the acetabular cup 20 because the outer surface 12 is in contact with the patient's bone causing the switch 18 to be positioned in the second, conductive state.

Although the embodiment illustrated in FIGS. 1-3 includes a single switch 18, the acetabular cup 20 may include any number of switches in other embodiments. Each switch may be used to detect whether a corresponding location of the outer surface 12 is in contact with the patient's bone to thereby determine proper seating of the cup 20. For example, in the embodiment illustrated in FIG. 4, the acetabular cup 20 includes four channels 50, 52, 54, 56, each similar to the channel 14, defined in the electrically conductive outer surface 12. An electrical conductor 60, 62, 64, 66, each similar to the electrical conductor 16, is positioned in each respective channel 50, 52, 54, 56. Each electrical conductors 60, 62, 64, 66 includes a respective first end 70, 72, 74, 76 extending from the respective channel 50, 52, 54, 56 at the rim 26 of the outer surface 12. Additionally, each electrical conductor 60, 62, 64, 66 includes a respective second end 80, 82, 84, 86, each of which forms a respective switch 90, 92, 94, 96 in the manner described above in regard to switch 18. Although the channels 50, 52, 54, 56 are defined in the outer surface 12 in a symmetrical pattern in the embodiment illustrated in FIG. 4, it should be appreciated that the channels 50, 52, 54, 56 may be defined in any orientation relative to each other in other embodiments such that a corresponding switch 18, 90, 92, 94, 96 may be defined at any location of the outer surface 12.

Figure 5:
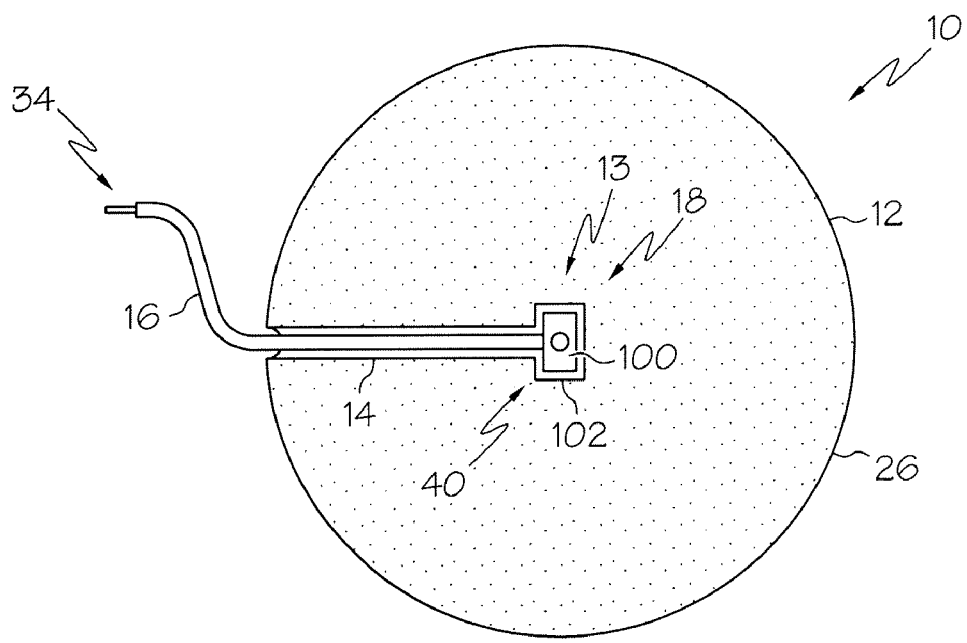
FIG. 5 is a plan view of the outer surface of another embodiment of the orthopaedic prosthesis of FIG. 1.
Figure 6:
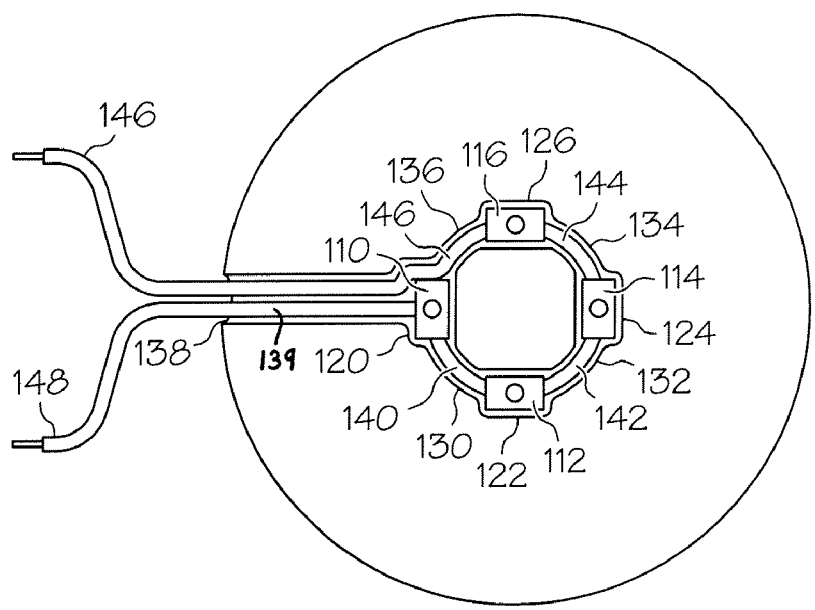
FIG. 6 is a plan view of the outer surface of another embodiment of the orthopaedic prosthesis of FIG. 1.

In some embodiments, the switch 18 may be embodied as a complex switch. For example, in some embodiments, as illustrated in FIGS. 5 and 6, the switch 18 may be embodied as a push-button switch 100. The push-button switch 100 may be embodied as any type of push-button switch. For example, the push-button switch 100 may be a plunger-type switch having a plunger configured to be depressed when the switch contacts the patient's bone. Alternatively, the push-button switch 100 may be a dome-type switch having a dome or ceiling configured to be collapsed when the switch contacts the patient's bone. Regardless, the push-button switch 100 is positioned in a recessed area 102 defined in the outer surface 12 of the acetabular cup 20 at the predetermined location 13. The push-button switch 100 may be secured in the recessed area 102 using any suitable adhesive or connector. In such embodiments, the channel 14 extends from the rim 26 of the outer surface 12 to the recessed area 102.

The push-button switch 100 is electrically coupled to the electrical conductor 16 and to the electrically conductive outer surface 12. As discussed above in regard to the switch 18, the push-button switch 100 includes two states, a non-conductive state and a conductive state. In the first state, no electrical connection is established between the electrical conductor 16 and the outer surface 12. In the second state, the switch 100 is activated (e.g., the switch 100 contacts a portion of the patient's bone) and an electrical connection is established between the electrical conductor 16 and the outer surface 12.

As discussed above, the acetabular cup 20 may include any number of switches 18, 100 to detect whether corresponding locations of the outer surface are in contact with the patient's bone. For example, as illustrated in FIG. 6, the acetabular cup 20 may include four push-button switches 110, 112, 114, 116 positioned in respective recessed areas 120, 122, 124, 126. In such embodiments, the outer surface 12 includes a number of channels 130, 132, 134, 136 connecting each of the recessed areas 120, 122, 124, 126. The channel 130 extends from the recessed area 120 to the recessed area 122. The channel 132 extends from the recessed area 122 to the recessed area 124. The channel 134 extends from the recessed area 124 to the recessed area 126. The channel 136 extends from the recessed area 126 to the recessed area 120. Additionally, a channel 138 extends from the rim 26 of the electrically conductive outer surface 12 to the recessed area 120. An electrical conductor 139 is positioned in the channel 138 and is electrically coupled to the push-button switch 110. An electrical conductor 140 is positioned in the channel 130 and is electrically coupled to the switches 110, 112. An electrical conductor 142 is positioned in the channel 132 and is electrically coupled to the switches 112, 114. An electrical conductor 144 is positioned in the channel 134 and is electrically coupled to the switches 114, 116. An electrical conductor 146 is positioned in the channel 136 and is electrically coupled to the switch 116. The electrical conductor 146 extends from the channel 136, through the channel 138, and extends out of the channel 138 at the rim 26 of the electrically conductive outer surface 12.

It should be appreciated that the embodiment of FIG. 6, includes two conductors 140, 146 extending out of the channel 138. In such embodiments, the switches 110, 112, 114, 116 are not electrically coupled to the outer surface 12. Additionally, the outer surface 12 may or may not be electrically conductive. For example, in the illustrative embodiment of FIG. 6, the outer surface 12 is not electrically conductive. In such embodiments, each of the switches 110, 112, 114, 116 either complete or break the electrical path defined by the electrical conductors 140, 142, 144, 146, 148. That is, each switch 110, 112, 114, 116 has a first state in which the electrical path defined by the electrical conductors 140, 142, 144, 146, 148 is broken and a second state in which the electrical path is completed. As such, as discussed in more detail below, an orthopaedic surgeon may determine whether the acetabular cup 20 is properly seated in such embodiments by measuring the continuity (or resistance) of the electrical path defined by the electrical conductors 140, 142, 144, 146, 148. Proper seating of the acetabular cup 20 is indicated when the electrical path is completed or broken depending on the type of switches 110, 112, 114, 116 used (i.e., the switches may be normally-open or normally-closed).

Although the acetabular cup 20 illustrated in FIG. 6 includes four separate switches 110, 112, 114, 116, the cup 20 may include a greater or smaller number of switches in other embodiments. For example, in some embodiments, the acetabular cup 20 may include a single switch similar to the embodiment illustrated in FIG. 5. However, because the single switch is not coupled to the outer surface 12 in such embodiments, an additional electrical conductor is included and extends out of the channel 14. Additionally, as discussed above in regard to FIG. 6, the outer surface 12 may not be electrically conductive in such embodiments. However, in other embodiments, the outer surface 12 may be electrically conductive and each switch 110, 112, 114, 116 may be electrically coupled to the electrically conductive outer surface 12. In such embodiments, the acetabular cup 20 includes a separate channel and electrical conductor for each switch similar to the embodiment illustrated in and described above in regard to FIG. 4.

Figure 7:
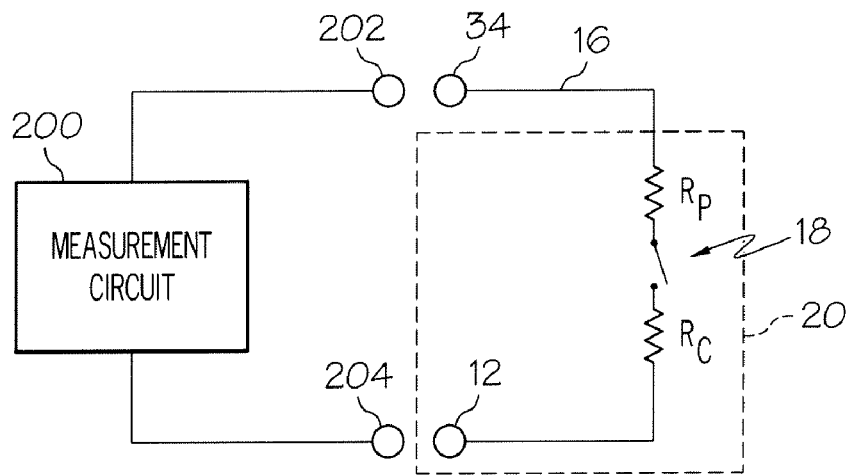
FIG. 7 is a simplified block diagram of one embodiment of a measuring circuit for determining proper seating of an orthopedic prosthesis having a seating indicator.

Referring now to FIG. 7, an orthopaedic surgeon may determine whether the acetabular cup 20 is properly seated by measuring the resistance between the electrical conductor 16 (or conductors 60, 62, 64, 66 in the embodiment of FIG. 4) and the electrically conductive outer surface 12 of the cup (or between two conductors in the embodiment of FIG. 6). To do so, a measurement circuit 200 may be used. The measurement circuit 200 may be embodied as any type of circuit or device capable of measuring the resistance or impedance of a circuit. The measurement circuit 200 includes a first measurement probe 202, which is electrically coupled to the first end 34 of the electrical conductor 16. The measurement circuit 200 also includes a second measurement probe 204, which is electrically coupled to the electrically conductive outer surface 12 of the acetabular cup 20 (or the other electrical conductor in the embodiment of FIG. 6). The measurement circuit 200 measures the resistance between the these two points. A measured resistance below a predetermined threshold is indicative that the switch 18 has been positioned in the second state (i.e., the predetermined location 13 has contacted the patient's bone) and the acetabular cup 20 is properly positioned. As shown in FIG. 7, the predetermined resistance threshold includes or otherwise accounts for the resistance of the electrical conductor 16, Rp, and the resistance of the outer surface 12, Rc.

Figure 8:
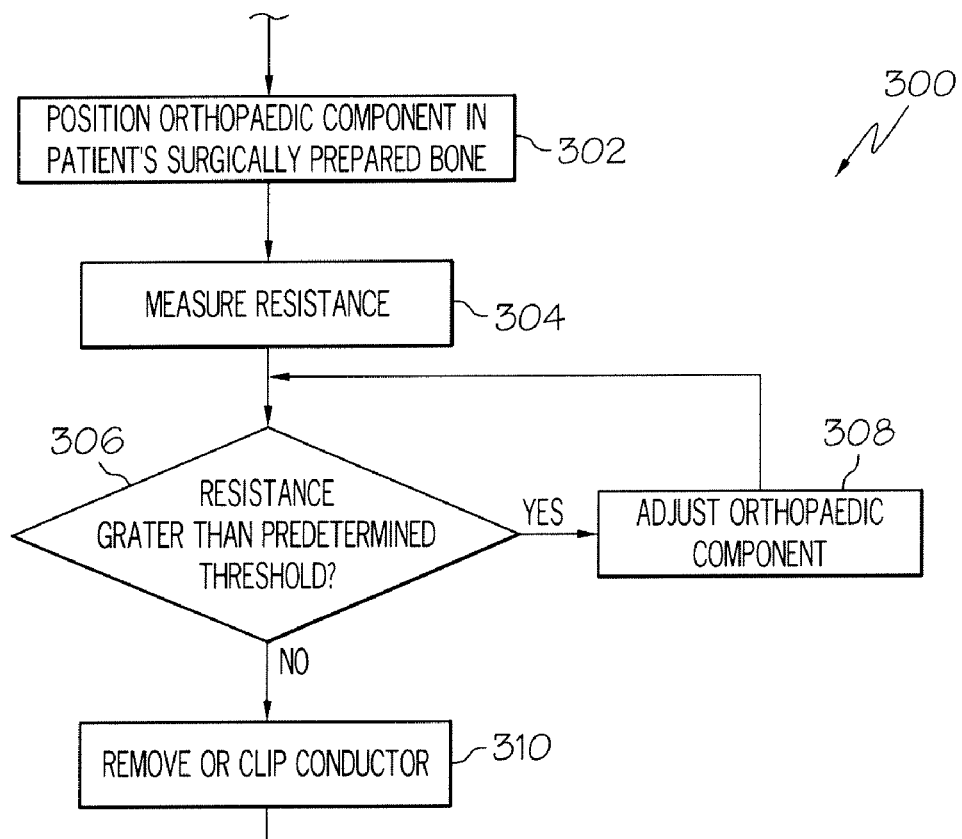
FIG. 8 is a simplified flowchart of a method for determining whether an orthopaedic prosthesis is seated.

Referring now to FIG. 8, a method 300 for determining whether the orthopaedic prosthesis 10 is properly seated begins with step 302. In step 302, the orthopaedic prosthesis 10 is positioned in the surgically-prepared bone of the patient. For example, in embodiments wherein the prosthesis 10 is embodied as the acetabular cup 20, the cup 20 is positioned in the patient's surgically-prepared acetabulum. After the prosthesis 10 has been so positioned, the orthopaedic surgeon measures the resistance between the electrical conductor 16 and the electrically conductive outer surface 12 of the acetabular cup 20 (or between the two electrical conductors in embodiments similar to the embodiment of FIG. 6) in step 304. In step 306, the measured resistance value is compared to the predetermined resistance threshold value. If the measured value is greater than the predetermined resistance threshold value, the position of the orthopaedic prosthesis 10 is adjusted in step 308. Additionally, in some embodiments, the bone of the patient may be re-shaped again in step 308. For example, in embodiments wherein the prosthesis 10 is embodied as an acetabular cup 20, the acetabulum of the patient may be re-reamed in step 308 to provide a better match to the acetabular cup 20. The resistance between the electrical conductor 16 and the outer surface 12 is again measured in step 306. If, however, the measured resistance is determined to be less than the predetermined resistance threshold in step 306, the orthopaedic prosthesis is considered to be properly seated. As such, the orthopaedic surgeon may trim or remove the electrical conductor 16. For example, in embodiments wherein the electrical conductor 16 is secured in the channel 14 via frictional forces, the orthopaedic surgeon may remove the electrical conductor 16 from the channel 14 by pulling on the end 34 of the electrical conductor 16.

Figure 9:
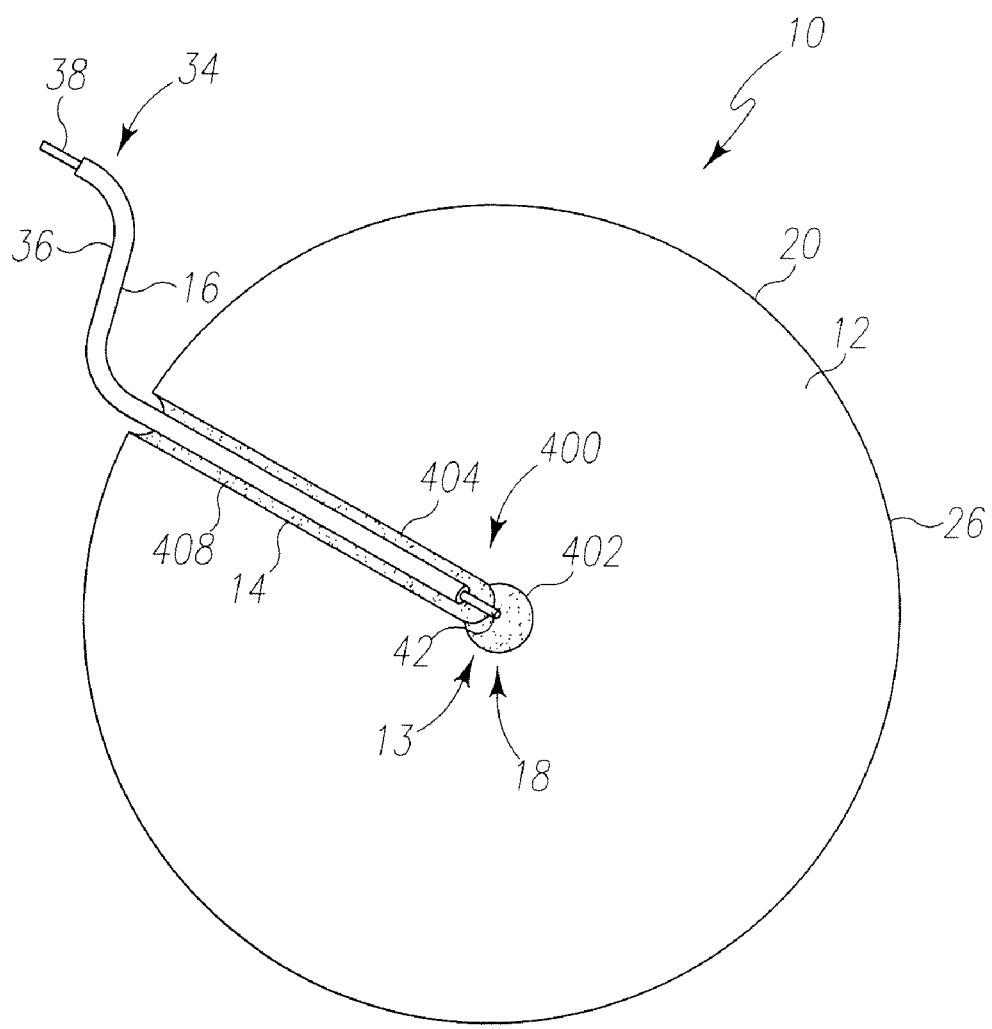
FIG. 9 is a plan view of the outer surface of another embodiment of the orthopaedic prosthesis of FIG. 1.
Figure 10:
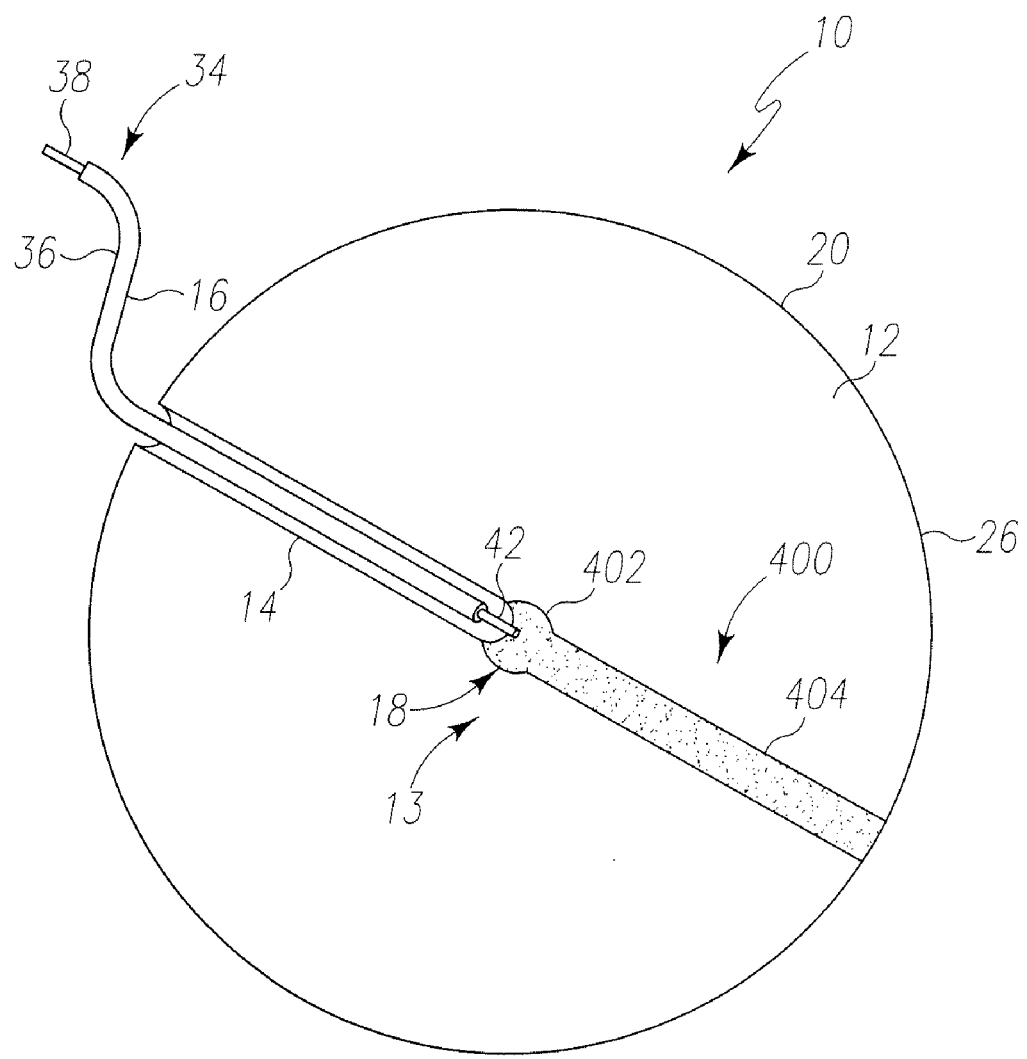
FIG. 10 is a plan view of the outer surface of another embodiment of the orthopaedic prosthesis of FIG. 1.

It should be appreciated that while the outer surface 12 has been described in the embodiments above as electrically conductive, only a portion of the outer surface 12 may be electrically conductive in other embodiments. For example, as illustrated in FIGS. 9 and 10, the outer surface 12 may include an electrically conductive trace or coating 400. In such embodiments, the areas of the outer surface 12 not covered by the trace 400 may be electrically non-conductive. For example, the acetabular cup 20 may be formed from an electrically non-conductive material, such as a ceramic or polymer material. The trace 400 may be embodied as an electrically conductive coating or texture applied to the outer surface 12 so as to form the electrically conductive trace 400.

In the illustrative embodiments of FIGS. 9 and 10, the electrically conductive trace 400 includes an electrically conductive pad 402 and an elongated electrically conductive trace 404 electrically coupled to the pad 402. The electrically conductive pad 402 is located at the predetermined location 13 on the outer surface 12. The pad 402 may have any shape and size capable of being contacted by the end 42 of the inner core 38 of the electrical conductor 16. In this way, the end 42 and the electrically conductive pad 402 form the switch 18. As discussed in detail above, the switch 18 includes two states, a non-conductive state and a conductive state. In the first state, the end 42 of the inner core 38 is spaced apart from the electrically conductive pad 402 and no electrical connection is established between the electrical conductor 16 and the electrically conductive trace 400. The switch 18 is positioned in the first state prior to implantation of the acetabular cup 20. In the second state, the end 42 of the inner core 38 is in contact with the electrically conductive pad 402 and an electrical connection is established between the electrical conductor 16 and the electrically conductive trace 400.

The elongated, electrically conductive trace 404 extends from the electrically conductive pad 402 toward the rim 26 of the outer surface 12. In some embodiments, the electrically conductive trace 404 may extend to the rim 26 of the outer surface 12. However, in other embodiments, the trace 404 may end short of the rim 26 while still being accessible by the orthopaedic surgeon when the acetabular cup 20 is implanted in the patient. In the particular embodiment illustrated in FIG. 9, the electrically conductive trace 404 is defined or otherwise formed in the channel 14. For example, an inner surface 408 of the outer surface 12 that defines the channel 14 may be coated with an electrically conductive material to form the trace 404. As such, the channel 14 houses the electrical conductor 16 while also forming an electrical conduit to the pad 402. However, in other embodiments, the electrically conductive trace 404 may be defined in locations on the outer surface 12 other than the channel 14. For example, as illustrated in FIG. 10, the electrically conductive trace 404 may extend from the electrically conductive pad 402 toward the rim 26 along a relatively straight or curved path separate form the channel 14.

In use, as discussed above, an orthopaedic surgeon may determine whether the orthopaedic prosthesis 10 (e.g., acetabular cup 20) is properly seated (i.e., whether the predetermined location 13 of the outer surface 12 is pressed against the patient's bone) by measuring the resistance, impedance, reactance, capacitance, inductance, or other circuit parameter between the inner core 38 of the electrical conductor 16 and the conductive trace 400. A measured circuit parameter value having a predetermined relationship with a predetermined threshold value (e.g., the measured circuit parameter is greater or lesser than the predetermined threshold value) is indicative of proper seating of the orthopaedic prosthesis 10 because the outer surface 12 is pressed against the patient's bone causing the switch 18 to be positioned in the second, conductive state.

Figure 11:
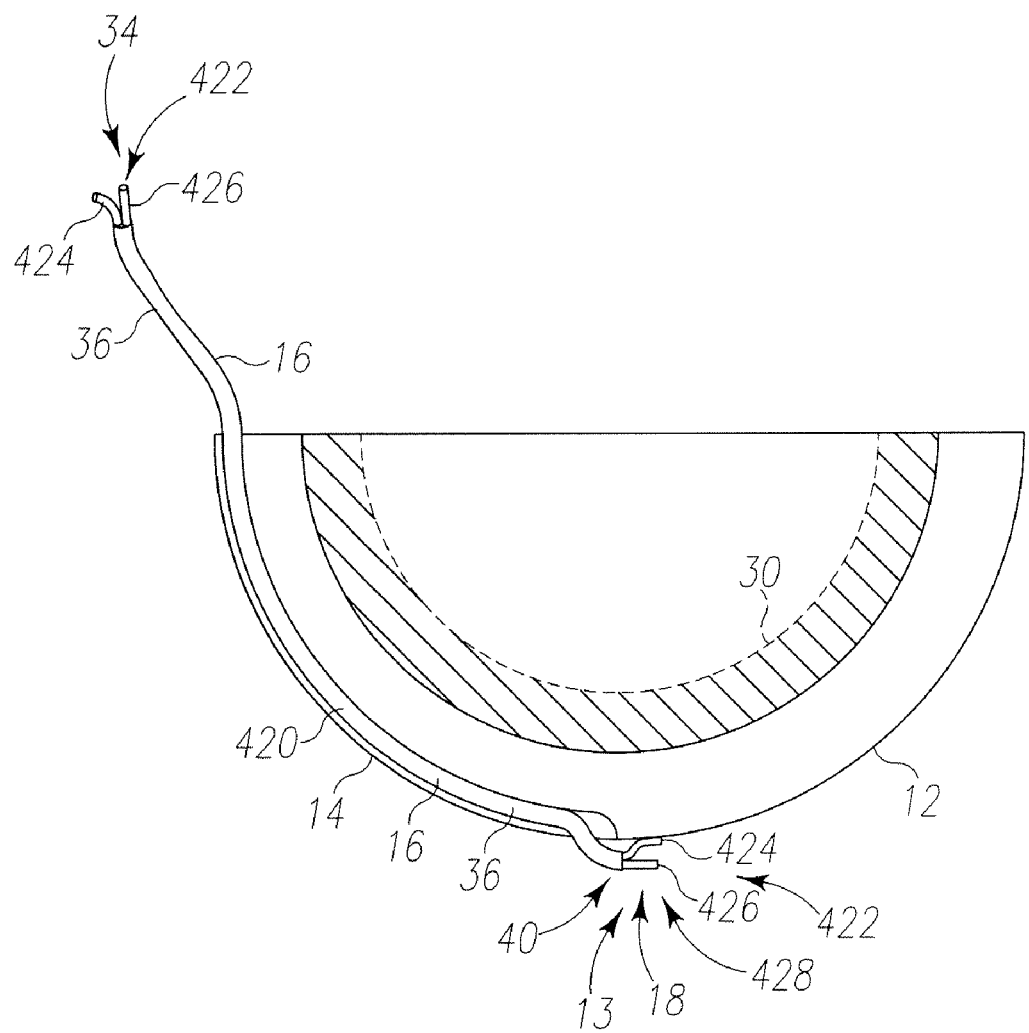
FIG. 11 is a cross-sectional view of another embodiment of the orthopaedic prosthesis of FIG. 1.

Referring now to FIG. 11, in some embodiments, the electrical conductor 16 may have more than one internal, electrical conductor (e.g., inner core 38). For example, in some embodiments the electrical conductor 16 may be embodied as an electrical conductor assembly 420 having multiple electrical conductors 422. The illustrative assembly 420 of FIG. 11 includes two internal, electrical conductors 424, 426 but may include additional electrical conductors in other embodiments. In some embodiments, the electrical conductors 424, 426 are embodied as separate, inner core conductors. However, in other embodiments, one of the electrical conductors 424, 426 may be embodied as an inner core conductor and the other electrical conductor 424, 426 may be embodied as a shielding wire or mesh (e.g., a coaxial wire). Each of the electrical conductors 424, 426 includes an end 428 at the second end 40 of the electrical conductor assembly 420. The ends 428 of the electrical conductors 424, 426 extend out of the channel 14 at the predetermined location 13 and are spaced apart from each other to form the switch 18. In some embodiments, one of the conductors 424, 426 (e.g., the shielding conductor) is attached or otherwise secured to the outer surface 12 at the predetermined location 13 to secure the end 428 of conductor 424, 426 in a fixed position. For example, the end of the secured conductor 424, 426 may form an electrically conductive pad.

As discussed above, the ends 428 of the electrical conductors 424, 426 form the switch 18, which includes two states, a non-conductive state and a conductive state. In the first state, the ends 428 of the electrical conductors 424, 426 are spaced apart from each other and no electrical connection is established between the electrical conductor 424 and the electrical conductor 426. The switch 18 is positioned in the first state prior to implantation of the acetabular cup 20. In the second state, the ends 428 of the electrical conductors 424, 426 are in contact with each other an electrical connection is established between the electrical conductor 16 and the electrically conductive trace 400. As such, an orthopaedic surgeon may determine whether the orthopaedic prosthesis 10 (e.g., acetabular cup 20) is properly seated (i.e., whether the predetermined location 13 of the outer surface 12 is pressed against the patient's bone) by measuring the resistance, impedance, reactance, capacitance, inductance, or other circuit parameter between the electrical conductors 424, 426 at the first end 34 of the electrical conductor assembly 420.

Figure 12:
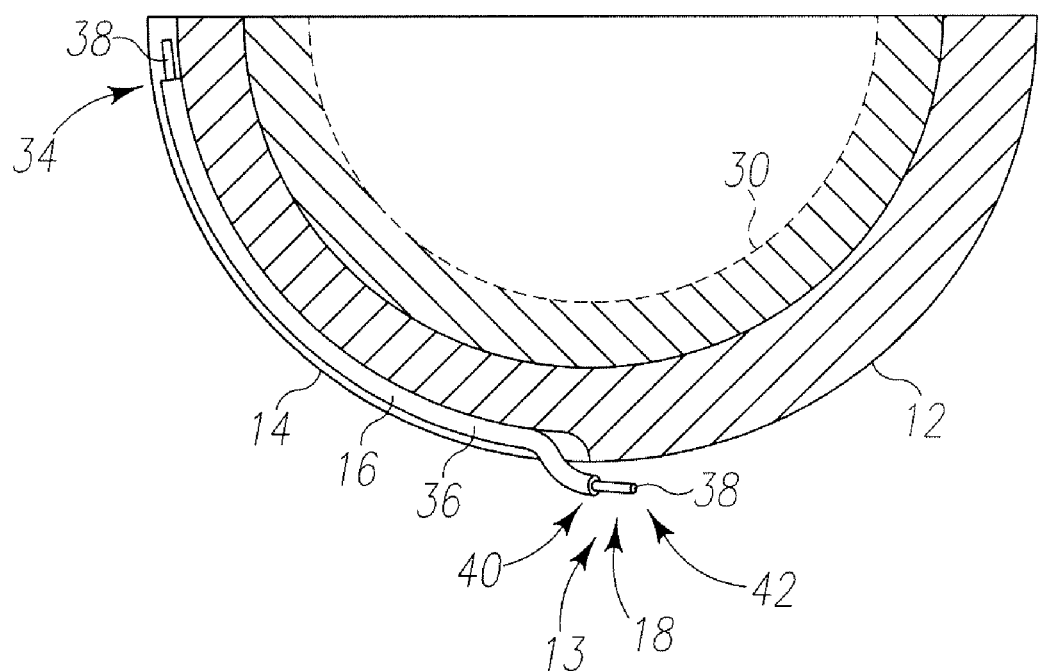
FIG. 12 is a cross-sectional view of another embodiment of the orthopaedic prosthesis of FIG. 1.

It should be appreciated that in each of the embodiments described above, the first end 34 of the electrical conductor 16, 420 extends out of a distal end of the channel 14 at the rim 26 of the curved outer surface 12. However, in other embodiments, the first end 34 of the electrical conductor 16, 420 may be located or otherwise remain in the channel 14 as illustrated in FIG. 12. In such embodiments, the channel 14 may or may not extend to the rim 26 of the curved outer surface 12. Although the electrical conductor 16, 420 does not extend out of the channel 14, the conductor 16, 420 is accessible by the orthopaedic surgeon to determine proper seating of the acetabular cup 20 as discussed above. For example, in some embodiments, the rim 26 of the curved outer surface 12 may be positioned above the acetabular margin of the patient's acetabulum such that the electrical conductor 16, 420 is accessible by the surgeon. During the measurement of the circuit parameter to determine proper seating of the orthopaedic prosthesis 10, the orthopaedic surgeon may lift the electrical conductor 16, 420 from the channel 14 if such repositioning of the electrical conductor 16, 420 is required. Additionally, after the acetabular cup 20 has been properly positioned, the electrical conductor 16, 420 may be removed from the channel 14 by the orthopaedic surgeon in the manner described above.

Figure 13:
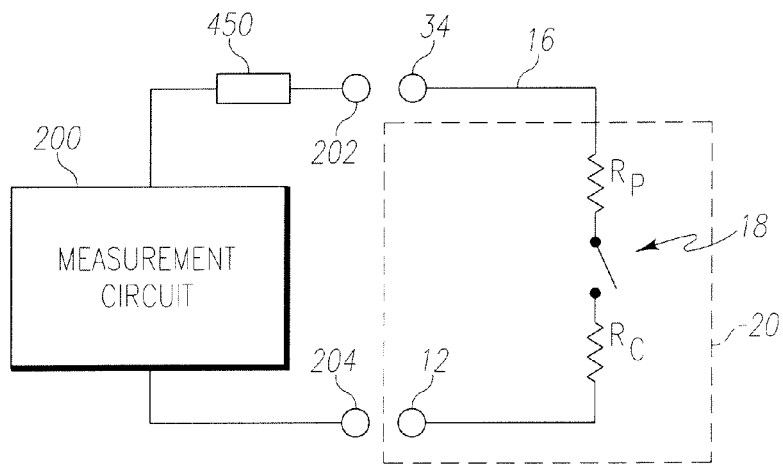
FIG. 13 is a simplified block diagram of another embodiment of a measuring circuit for determining proper seating of an orthopedic prosthesis having a seating indicator.

Referring now to FIG. 13, an orthopaedic surgeon may determine whether the orthopaedic prosthesis 10 (e.g., the acetabular cup 20) is properly seated by measuring a circuit parameter of the circuit formed by the electrical conductor 16 and the electrically conductive outer surface 12 or electrically conductive trace 400 or by the multiple electrical conductors 424, 426 of the electrical assembly 420, depending on the particular embodiment. The particular circuit parameter measured may be embodied as any type of circuit parameter capable of determining whether the switch 18 is in the first, non-conductive state or the second, conductive state. For example, the circuit parameter may be embodied as resistance, impedance, reactance, capacitance, inductance, resistor-capacitor (RC) time constant, or other circuit parameter.

Figure 14:
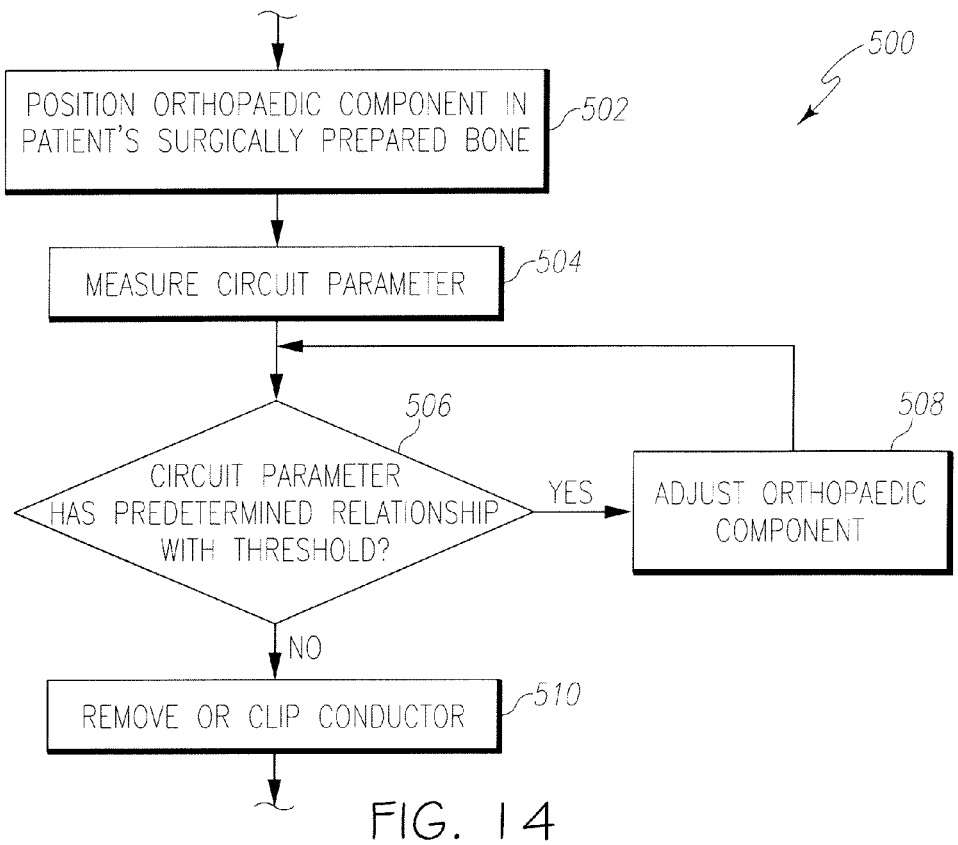
FIG. 14 is a simplified flowchart of another method for determining whether an orthopaedic prosthesis is seated.

As shown in FIG. 13, in some embodiments, the measurement circuit 200 may include a circuit device 450 for measuring a circuit. The type of circuit device 450 used may depend on the particular circuit parameter to be measured. For example, in one particular embodiment, the circuit device 450 is embodied as a capacitor and the measurement circuit 200 is configured to determine the state of the switch 18 based on the RC constant of the circuit formed by the electrical conductor 16, 420 and the electrical outer surface 12 or trace 400. In such embodiments, the resistor of the RC circuit may be embodied as, or otherwise include, the resistance of the electrical conductor 16, Rp, and the resistance of the outer surface 12, Rc. In some embodiments, an additional resistor may be used. The circuit device 450 may form a portion of the measurement circuit 200 or may be included in the electrical conductor 16, 420 (e.g., positioned inline with the electrical conductors). As such, it should be appreciated that the conductive state of the switch 18, and thereby the proper seating of the orthopaedic prosthesis 10, may be determined using any suitable circuit parameter including, but not limited to resistance, impedance, reactance, capacitance, inductance, and RC time constant, Referring now to FIG. 14, a method 500 for determining whether the orthopaedic prosthesis 10 is properly seated begins with step 502. In step 502, the orthopaedic prosthesis 10 is positioned in the surgically-prepared bone of the patient. For example, in embodiments wherein the prosthesis 10 is embodied as the acetabular cup 20, the cup 20 is positioned in the patient's surgically-prepared acetabulum. After the prosthesis 10 has been so positioned, the orthopaedic surgeon measures the circuit parameter of the circuit attached to the prosthesis 10 (step 504), which is formed by the electrical conductor 16 and the electrically conductive outer surface 12 or electrically conductive trace 400 or by the multiple electrical conductors 424, 426 of the electrical assembly 420, depending on the particular embodiment. In step 506, the measured circuit parameter is compared to a predetermined threshold value, and proper seating of the orthopaedic prostheses 10 is determined based on whether the measured circuit parameter has a predetermined relationship with the threshold value. For example, in embodiments wherein the measured circuit parameter is embodied as resistance or impedance of the circuit, the measured circuit parameter may be compared to a predetermined resistance or impedance value in step 506 and proper seating of the orthopaedic prosthesis may be verified if the measured resistance/impedance is below a the predetermined threshold resistance/impedance.

If the measured circuit parameter does not have the predetermined relationship with the threshold value, the position of the orthopaedic prosthesis 10 is adjusted in step 508. Additionally, in some embodiments, the bone of the patient may be re-shaped again in step 508. For example, in embodiments wherein the prosthesis 10 is embodied as an acetabular cup 20, the acetabulum of the patient may be re-reamed in step 508 to provide a better match to the acetabular cup 20. The circuit parameter is subsequently again measured in step 306. If, however, the measured circuit parameter does have the predetermined relationship with the threshold value (e.g., is less than or greater than the threshold value) the orthopaedic prosthesis 10 is considered to be properly seated. As such, the orthopaedic surgeon may trim or remove the electrical conductor 16, 420 in step 510.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the devices, systems, and methods described herein. It will be noted that alternative embodiments of the devices, systems, and methods of the present disclosure may not include all of the features described yet still benefit from at least some of the advantages of such features. Those of ordinary skill in the art may readily devise their own implementations of the devices, systems, and methods that incorporate one or more of the features of the present invention and fall within the spirit and scope of the present disclosure as defined by the appended claims.

The invention claimed is:

1. An acetabular cup comprising:
   an outer surface configured to confront a portion of a patient's acetabulum when the acetabular cup is implanted in the patient, the outer surface including a channel defined therein;
   an electrical conductor positioned in the channel;
   an electrically conductive trace formed on the outer surface; and
   a switch located at a first location on the outer surface, the switch having a first state wherein an electrical connection between the electrical conductor and the electrically conductive trace is broken and a second state wherein an electrical connection between the electrical conductor and the electrically conductive trace is established.

2. The acetabular cup of claim 1, wherein the electrically conductive trace is located in the channel of the outer surface.

3. The acetabular cup of claim 1, wherein the electrically conductive trace comprises an electrically conductive pad formed on the outer surface at the first location.

4. The acetabular cup of claim 1, wherein the electrically conductive trace extends from the first location to a rim of the outer surface.

5. The acetabular cup of claim 1, wherein the electrical conductor has a first end located in the channel toward a rim of the outer surface.

6. The acetabular cup of claim 5, wherein the switch comprises a second end of the electrical conductor, the second end of the electrical conductor extending out of the channel at the first location of the outer surface and positionable such that the second end comes into contact with the electrically conductive trace when the first location of the outer surface is pressed against the patient's acetabulum.

7. The acetabular cup of claim 1, wherein the switch is configured such that the switch is positioned in the second state when the first location of the outer surface is pressed against the patient's acetabulum.

8. The acetabular cup of claim 1, wherein the switch comprises a push-button switch, the push-button switch being biased to the first state.

9. The acetabular cup of claim 8, wherein the push-button switch is configured such that the push-button switch is positioned in the second state when the first location of the outer surface is pressed against the patient's acetabulum.

10. The acetabular cup of claim 1, wherein the channel extends from the first location to a rim of the outer surface.

11. An acetabular cup comprising:

an outer surface configured to confront a portion of a patient's acetabulum when the acetabular cup is implanted in the patient, the outer surface including a channel defined therein;

an electrical conductor assembly positioned in the channel, the electrical conductor assembly including a first conductor and a second conductor, each of the first and second conductors having an end extending out of the channel at a first location on the outer surface, the ends of the first and second conductors forming a switch having a first state wherein an electrical connection between the first and second conductors is broken and a second state wherein an electrical connection between the first and second conductors is established.

12. The acetabular cup of claim 11, wherein the second conductor is secured to the outer surface at the first location.

13. The acetabular cup of claim 12, wherein the outer surface includes an electrically conductive pad formed thereon, the second conductor being electrically connected to the electrically conductive pad.

14. The acetabular cup of claim 11, wherein each end of the first and second conductor comprises a second end, and wherein each of the first and second conductors includes a first end opposite the second end, the first ends of the first and second conductors being located in the channel.

15. The acetabular cup of claim 11, wherein the switch is configured such that the switch is positioned in the second state when the first location of the outer surface is pressed against the patient's acetabulum.

16. An acetabular cup comprising:

an outer surface configured to confront a portion of a patient's acetabulum when the acetabular cup is implanted in the patient, the outer surface including a channel defined therein;

an electrical conductor assembly positioned in the channel, the electrical conductor assembly including a first conductor and a second conductor, each of the first and second conductors having an end extending out of the channel at a first location on the outer surface, the ends of the first and second conductors forming a switch having a first state wherein an electrical connection between the first and second conductors is broken and a second state wherein an electrical connection between the first and second conductors is established, wherein the first conductor comprises a wire and the second conductor comprises a shielding formed around the wire.

* * * * *